(12) United States Patent
Kimura et al.

(10) Patent No.: US 6,794,383 B2
(45) Date of Patent: Sep. 21, 2004

(54) HEART MUSCULAR CELL APOPTOSIS INHIBITORS AND REMEDIES/PREVENTIVES FOR HEART DISEASES

(75) Inventors: Haruhide Kimura, Tsukuba (JP); Seiichi Tanida, Nagaokayo (JP); Tatsuhiko Kaneko, Osaka (JP)

(73) Assignee: Takeda Chemical Industries, Ltd., Osaka (JP)

(*) Notice: Subject to any disclaimer, the term of this patent is extended or adjusted under 35 U.S.C. 154(b) by 0 days.

(21) Appl. No.: 10/363,290

(22) PCT Filed: Aug. 30, 2001

(86) PCT No.: PCT/JP01/07468
§ 371 (c)(1),
(2), (4) Date: Feb. 27, 2003

(87) PCT Pub. No.: WO02/18356
PCT Pub. Date: Mar. 7, 2002

(65) Prior Publication Data
US 2003/0186971 A1 Oct. 2, 2003

(30) Foreign Application Priority Data
Aug. 31, 2000 (JP) ........................................ 2000-262757

(51) Int. Cl.$^7$ ............................................ A61K 31/5415
(52) U.S. Cl. ........................................ 514/224.2; 544/50
(58) Field of Search ........................... 514/224.2; 544/50

(56) References Cited

U.S. PATENT DOCUMENTS 3,470,168 A    9/1969    Wolf et al. .................. 260/243

FOREIGN PATENT DOCUMENTS

| EP | 0566018 | 10/1993 |
| WO | WO 99/11624 | 3/1999 |
| WO | WO 99/11624 A | 3/1999 |
| WO | WO 02/44157 A3 | 6/2002 |
| WO | WO 02/44157 A2 | 6/2002 |

OTHER PUBLICATIONS

Conti, L., et al., "Su alcune aril–cheto–benzo–m–tiazine" *Istituto Di Chimica Industriale Dell Universita Di Bologna*, vol. 15, (1957), pp. 37–39.
Conti, L., et al., "Ricerche sullie tiazine: benzo–cheto–m––tiazine e alcuni suoi 2–(alchilamino–metil)–derivati", *Instituto Di Chimica Organica Dell Universita Di Barl*, vol. 18, (1959), pp. 29–33.
Salzinger, G., "Heterocyclen durch Reaktion von Mercapto–und Hydroxycarbon–saureestern mit aklivierten Nitrilen", *Liebigs Annalen Der Chemie*, (1978) pp. 473–511.
Sheu, S–Y, et al., "Inhibition of Xanthine Oxidase by Benzothiazinone Analogues" *Anticancer Research*, vol. 19, No. 1A, (1999), pp. 119–123.
Chemical Abstracts 51: 17927–17930 (1957).
Ibrahim, et al. "Nitriles Heterocylic Synthesis: A New Approach for The Synthesis of Thiazinones" 22(8): 1677–1683 (1984).

*Primary Examiner*—Richard L. Raymond
(74) *Attorney, Agent, or Firm*—Elaine M. Ramesh; Mark Chao

(57) ABSTRACT

The present invention is intended to provide excellent preventives and/or remedies for heart diseases. Specifically, the present invention provides heart muscle cell apoptosis inhibitors, preventives and/or remedies for heart diseases, comprising a compound represented by the following formula:

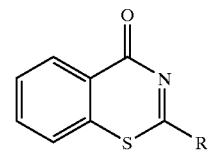

wherein R represents an optionally substituted hydrocarbon group, an optionally substituted aromatic heterocyclic group, or an optionally substituted amino group; or a salt thereof.

16 Claims, 1 Drawing Sheet

HEART MUSCULAR CELL APOPTOSIS INHIBITORS AND REMEDIES/ PREVENTIVES FOR HEART DISEASES

This application is the National Phase filing of International Patent Application No. PCT/JP01/07468, filed Aug. 30, 2001.

TECHNICAL FIELD

This invention relates to an inhibitor of heart muscule cell apoptosis, and a prophylactic and/or therapeutic agent for heart diseases.

BACKGROUND ART

In recent years, it has been revealed that apoptosis is closely invloved in onset or progress of various heart diseases (R. Sanders Williams, The New England Journal of Medicine, vol. 341, p. 759, 1999).

Apoptosis is closely invloved in morphognesis and histogenesis in the development process, maintenance of homeostasis, and bio-defence, and it is cell death having an important role in maintaining individual lifes. When the death process regulated by genes is congenitally or postnatally hindered, apoptosis is excessively induced or inhibited to cause functional disorders in various organs, and thus diseases (Shin Yonehara, Saishin Igaku, vol. 54, p. 825, 1999).

In a mammalian heart, it is considered that heart muscle cells are finally differentiated cells, and lose proliferation activity. Accordingly, when heart muscle cells disappear by apoptosis, the heart contraction should be maintained only by remaining cells. Disappearance of heart muscle cells beyond threshold necessary for maintaining the heart contraction would result in abnormal heart functions and diseases. Apoptosis of heart muscle cells is actually observed in various animal models with cardiac insufficiency or in human patients with cardiac insufficiency, and it is noted that disappearance or lack of heart muscle cells by apoptosis may be involved in onset and progress of cardiac insufficiency (Narula, J. et al., The New England Journal of Medicine, vol. 335, p. 1182, 1996). It is further recognized that in heart muscle cells of human patients with cardiac insufficiency, an apoptosis-inhibitory factor Bcl-2 is expressed in excess, which is a possible compensation mechanism for cardiac insufficiency (Olivetti, G. et al., The New England Journal of Medicine, vol. 336, p. 1131, 1997); that serum levels of soluble Fas (sFas has an inhibitory activity on apoptosis) which lacks a membrane penetration domain in the Fas receptor known as an apoptosis inducing receptor, are increased significantly in proportion to severeness in NYHA class (New York Heart Association Functional Class) but independently of fundamental diseases, and thus an increase in serum levels of sFas is considered to be a compensatory mechanism to inhibit promotion of apoptosis in cardiac insufficiency (Nishigaki, K. et al., Journal of the American College of Cardiology, vol. 29, p. 1214, 1997); and that in the heart with dilation-type myocardiosis, deoxyribonuclease I (DNase I) considered as a indicator of apoptosis is increased 7-fold or more than in healthy persons (Yao, M. et al., Journal of Molecular & Cell Cardiology, vol. 28, p. 95, 1996).

Recent important findings related to protection of heart muscle cells include those from studies on mice with deficiency in gp130 specifically in the ventricle. As a result of analysis of the mice, it is revealed that the signal from gp130-mediated receptors (gp130 signal) play an important role in protecting the heart functions, and these studies draw attention as a new development of heart muscle cell-protective signals leading to therapy of heart diseases (Hirota, et al., Cell, vol. 97, p. 189, 1999, and Senior, K. Molecular Medicine Today, vol. 5, p. 283, 1999). Therefore, it is highly possible that a compound having an inhibitory action on apoptosis of heart muscle cells or an enhancing action on heart muscle cell-protective signals may serves as a new preventive and/or remedy for heart diseases.

When considered at the level of internal organs, the functions of the heart muscle are lowered in human cardiac diseases, and insufficient heart muscle contraction often endangers the maintenance of the life. Abnormalities, for example, myocardial disorders, abnormal heart pumping, pressure burden due to high blood pressure, volume burden due to acute nephritis, and insufficient blood pumping caused by these abnormalities lead to the onset of cardiac insufficiency. Against these abnormalities, the sympathetic nervous system, the internal secretion system, and the like work together to start a compensating mechanism, resulting in cardiac hypertrophy accompanied by hypertrophy of myocardial cells. However, when these abnormalities occur alone or in combination persistently and chronically, the hypertrophied myocardial cells are not sufficiently supplied with blood, and thus the myocardial cells disappear due to apoptosis, etc. As a result, the compensating mechanism fails to work, leading to a cardiac insufficiency syndrome accompanied by myocardial disorders such as insufficient heart contraction, a reduction in pumped blood, circulatory disorders in internal organs, venostasis, and body fluid retention. To treat these, amelioration of myocardial cell disorders, enhancement of the heart-protecting action, recovery from the reduced cardiac functions due to insufficient heart contraction, suppression of causative breakdown of compensation in vivo, or amelioration of the excessive compensation is necessary.

Incidentally, 2-substituted-4H-1,3-benzothiazin-4-one compounds such as 2-(2-pyridyl)-1,3-benzothiazin-4-one, 2-(3-pyridyl)-1,3-benzothiazin-4-one and 2-(4-pyridyl)-1,3-benzothiazin-4-one are described in Chemical Abstracts, vol.51, 17927g (1957), but any specific action thereof is not described. 2-ethoxycarbonylmethyl-1,3-benzothiazin-4-one is described in Heterocycles, vol.22, 1677–1682 (1984), but any action thereof is not described.

At present, the cardiac insufficiency syndrome is treated by using cardiotonic glycosides such as digoxin, sympathetic agents such as dobutamine, phosphodiesterase inhibitors such as amrinone, vasodilators such as hydralazine, calcium antagonist, angiotensin converting enzyme inhibitor and angiotensin receptor antagonist, and dilated cardiomyopathy is treated by β-blockers, etc. But for therapeutic methods for suppressing the excessive compensation and for suppressing breakdown of compensation including apoptosis, there are no reported pharmaceuticals entirely satisfactory in clinical use.

DISCLOSURE OF THE INVENTION

The present inventors found for the first time that a variety of 2-substituted-4H-1,3-benzothiazin-4-one compounds have an inhibitory action on heart muscle cell apoptosis. As a result of further investigation based on these findings, the present inventors achieved the present invention.

Thus, the present invention provides:

(1) An inhibitor of heart muscle cell apoptosis comprising a compound represented by the following formula:

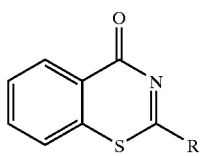

wherein R represents an optionally substituted hydrocarbon group, an optionally substituted aromatic heterocyclic group, or an optionally substituted amino group; or a salt thereof (referred to as Compound (I));

(2) The inhibitor of heart muscle cell apoptosis as described in (1), which is a prophylactic and/or therapeutic agent for heart diseases;

(3) The inhibitor of heart muscle cell apoptosis as described in (1), which is an enhancer of gp130 signal;

(4) The inhibitor of heart muscle cell apoptosis as described in (1), which is an enhancer of heart muscle cell protection signal;

(5) A pharmaceutical composition comprising Compound (I);

(6) A method for inhibiting heart muscle cell apoptosis in a mammal, comprising administrating an effective amount of Compound (I) to said mammal;

(7) Compound (I) which is used for inhibition of heart muscle cell apoptosis;

(8) Use of Compound (I) for production of an inhibitor of heart muscle cell apoptosis.

BEST MODE FOR CARRYING OUT THE INVENTION

Figure 1:
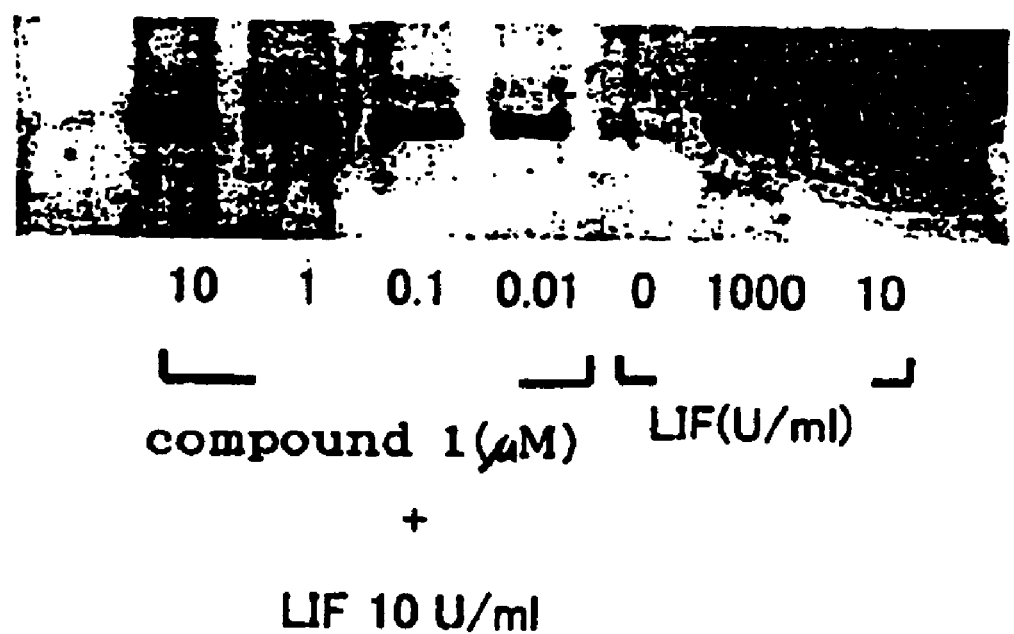
FIG. 1 shows the result of detection of phosphorylated STAT3 as described in Example 2

In the "optionally substituted hydrocarbon group" as represented by R in the formula above, the "hydrocarbon group" includes, e.g., alkyl, cycloalkyl, cycloalkylalkyl, alkenyl, alkynyl, aryl, aralkyl, etc.

The "alkyl" includes, for example, $C_{1-6}$ alkyl (e.g., methyl, ethyl, propyl, isopropyl, butyl, isobutyl, sec-butyl, tert-butyl, pentyl, hexyl, etc.), etc.

The "cycloalkyl" includes, for example, $C_{3-6}$ cycloalkyl (e.g., cyclopropyl, cyclobutyl, cyclopentyl, cyclohexyl, etc.), etc.

The "cycloalkylalkyl" includes, for example, $C_{4-7}$ cycloalkylalkyl groups (e.g., cyclopropylmethyl, cyclobutylmethyl, cyclopentylmethyl, cyclohexylmethyl, etc.), etc.

The "alkenyl" includes, for example, $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.), etc.

The "alkynyl" includes, for example, $C_{2-6}$ alkynyl (e.g., ethynyl, propargyl, 1-butynyl, 2-butynyl, 3-butynyl, 1-hexynyl, etc.), etc.

The "aryl" includes, for example, $C_{6-14}$ aryl (e.g., phenyl, naphthyl, biphenyl, indanyl, 1,2,3,4-tetrahydronaphthyl, etc.), etc.

The "aralkyl" includes, for example, $C_{7-16}$ aralkyl (e.g., benzyl, phenethyl, phenylpropyl, naphthylmethyl, indanylmethyl, etc.), etc.

In the "optionally substituted hydrocarbon group" as represented by R, examples of "substituent groups" include a halogen atom (e.g., fluorine, chlorine, bromine, iodine, etc.), an aromatic heterocyclic group, oxo, hydroxy, $C_{1-4}$ alkoxy (e.g., methoxy, ethoxy, propoxy, butoxy, etc.), carboxy, $C_{1-4}$ alkyl-carbonyl (e.g., acetyl, propionyl, etc.), $C_{6-14}$ aryl-carbonyl (e.g., benzoyl, etc.), $C_{1-4}$ alkoxy-carbonyl (e.g., methoxycarbonyl, ethoxycarbonyl, propoxycarbonyl, butoxycarbonyl, etc.), $C_{6-14}$ aryloxy-carbonyl (e.g., phenoxycarbonyl, etc.), $C_{7-16}$ aralkyloxy-carbonyl (e.g., benzyloxycarbonyl, etc.), carbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), optionally halogenated $C_{6-14}$ aryl-carbamoyl, 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), and optionally substituted 5- to 7-membered saturated cyclic amino-carbonyl, etc. Among these, $C_{6-14}$ aryl-carbonyl, $C_{1-4}$ alkoxy-carbonyl, 5- to 6-membered heterocyclic carbamoyl, and 5- to 7-membered saturated cyclic amino-carbonyl are preferred.

The "aromatic heterocyclic group" includes, for example, a monovalent group derived by removal of a hydrogen atom from a 5- to 14-membered (preferably 5- to 10-membered) aromatic heterocycle containing 1 to 4 heteroatoms of one or two species selected from a nitrogen atom, a sulfur atom and an oxygen atom in addition to the carbon atoms. The "5- to 14-membered (preferably 5- to 10-membered) aromatic heterocycle" includes, for example, aromatic heterocycles such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazol, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazane, phenoxazine, etc.; and rings formed by condensing any one of these rings (preferably monocycle) with one or more (preferably one or two) aromatic rings (e.g., benzene ring, etc.).

The "aromatic heterocyclic group" includes, for example, thienyl (e.g., 2-thienyl, 3-thienyl), furyl (e.g., 2-furyl, 3-furyl), pyridyl (e.g., 2-pyridyl, 3-pyridyl, 4-pyridyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 3-pyrrolyl), imidazolyl (e.g., 2-imidazolyl), pyridazinyl (e.g., 3-pyridazinyl), isothiazolyl (e.g., 3-isothiazolyl), isooxazolyl (e.g., 3-isooxazolyl), indolyl (e.g., 1-indolyl, 2-indolyl, 3-indolyl), benzothiazolyl (e.g., 2-benzothiazolyl), benzothienyl (e.g., 2-benzo[b]thienyl, 3-benzo[b]thienyl), benzofuranyl (e.g., 2-benzo[b]furanyl, 3-benzo[b]furanyl), etc. Among these, a 5- to 6-membered heterocyclic group containing 1 to 3 heteroatoms selected from a nitrogen atom, a sulfur atom and an oxygen atom in addition to the carbon atoms (e.g., pyridyl such as 2-pyridyl, 3-pyridyl, 4-pyridyl)) is preferred.

The "optionally halogenated $C_{6-14}$ aryl-carbamoyl" includes, for example, $C_{6-14}$ aryl-carbamoyl (e.g., phenyl carbamoyl, 1-naphthyl carbamoyl, 2-naphthyl carbamoyl, etc.) optionally substituted with 1 to 3 halogen atoms (e.g., fluorine, chlorine, etc.).

In the "optionally substituted 5- to 7-membered saturated cyclic amino-carbonyl", the "5- to 7-membered saturated cyclic amino-carbonyl" includes, for example, pyrrolidin-1-ylcarbonyl, piperidinocarbonyl, piperazin-1-ylcarbonyl, morpholinocarbonyl, etc. Examples of "substituent groups" in the "optionally substituted 5- to 7-membered saturated cyclic amino-carbonyl" include, for example, $C_{1-3}$ alkyl (e.g., methyl, etc.), phenyl, benzyl, etc.

The "optionally substituted hydrocarbon group" may have, for example, one to five, preferably one to three, of the above-mentioned substituent groups at substitutable positions. When the number of substituent groups is 2 or more, the respective substituent groups may be the same or different.

In the "optionally substituted aromatic heterocyclic group" as represented by R, the "aromatic heterocyclic group" includes, for example, a monovalent group derived by removal of a hydrogen atom from a 5- to 14-membered (preferably 5- to 10-membered) aromatic heterocycle containing 1 to 4 heteroatoms of one or two species selected from a nitrogen atom, a sulfur atom and an oxygen atom in addition to the carbon atoms. The "5- to 14-membered (preferably 5- to 10-membered) aromatic heterocycle" includes, for example, aromatic heterocycles such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazol, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazane, phenoxazine, etc.; and rings formed by condensing any one of these rings (preferably monocycle) with one or more (preferably one or two) aromatic rings (e.g., benzene ring, etc.).

The "aromatic heterocyclic group" includes, for example, thienyl (e.g., 2-thienyl, 3-thienyl), furyl (e.g., 2-furyl, 3-furyl), pyridyl (e.g., 2-pyridyl, 3-pyridyl, 4-pyridyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 3-pyrrolyl), imidazolyl (e.g., 2-imidazolyl), pyridazinyl (e.g., 3-pyridazinyl), isothiazolyl (e.g., 3-isothiazolyl), isooxazolyl (e.g., 3-isooxazolyl), indolyl (e.g., 1-indolyl, 2-indolyl, 3-indolyl), benzothiazolyl (e.g., 2-benzothiazolyl), benzothienyl (e.g., 2-benzo[b]thienyl, 3-benzo[b]thienyl), benzofuranyl (e.g., 2-benzo[b]furanyl, 3-benzo[b]furanyl), etc. Among these, a 5- to 6-membered heterocyclic group containing 1 to 3 heteroatoms selected from a nitrogen atom, a sulfur atom and an oxygen atom in addition to the carbon atoms (e.g., pyridyl such as 2-pyridyl, 3-pyridyl, 4-pyridyl)) is preferred.

In the "optionally substituted aromatic heterocyclic group" as represented by R, examples of "substituent group" include, for example, the same substituent groups as described above in the "optionally substituted hydrocarbon group". Among these substituent groups, for example, hydroxy is preferred.

The "optionally substituted amino group" as represented by R includes, for example, amino, guanidino, amino having a substituent group, guanidino having a substituent group, etc.

In the "amino having a substituent group" and "guanidino having a substituent group", the "substituent group" includes, for example, the "optionally substituted hydrocarbon group" as represented by R, etc.

Preferable examples of R include benzyl, benzoylmethyl, 3-pyridylaminocarbonylmethyl, 4-chlorophenylaminocarbonylmethyl, ethoxycarbonylmethyl, piperidinocarbonylmethyl, 2-pyridyl, 3-pyridyl, 4-pyridyl, 3-hydroxy-2-benzo[b]furanyl, guanidino, etc.

Further, Compound (I) can occur as a tautomer represented by the following formulas, or as a salt thereof:

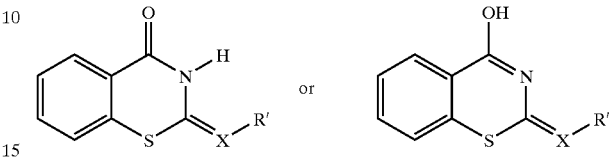

wherein X represents CH or a nitrogen atom, and R' represents a group derived by removal of X—H from R. Compound (I) includes the tautomer, a salt thereof, and a mixture thereof with Compound (I).

The salt of Compound (I) or its tautomer is preferably a pharmaceutically acceptable salt, and includes a salt with an inorganic base, a salt with an organic base, a salt with an inorganic acid, a salt with an organic acid, a salt with a basic or acidic amino acid and so on. The preferred examples of salts with an inorganic base include an alkali metal salt such as sodium salt, potassium salt; alkali earth metal salt, calcium salt and magnesium salt; and aluminum salt, ammonium salt, etc. The preferred examples of salts with an organic base include trimethylamine salt, triethylamine salt, pyridine salt, picoline salt, ethanolamine salt, diethanolamine salt, triethanolamine salt, dicyclohexylamine salt, N,N'-dibenzylethylenediamine salt, etc. The preferred examples of salts with an inorganic acid include a salt of hydrochloric acid, hydrobromic acid, nitric acid, sulfuric acid, phosphoric acid, etc. The preferred examples of salts with an organic acid include a salt of formic acid, acetic acid, propionic acid, fumaric acid, oxalic acid, tartaric acid, maleic acid, citric acid, succinic acid, malic acid, methanesulfonic acid, benzenesulfonic acid, benzoic acid, etc. The preferred examples of salts with a basic amino acid include a salt with arginine, lysine, ornithine, etc. The preferred examples of salts with an acidic amino acid include a salt with aspartic acid, glutamic acid, etc.

Compound (I) may be commercially purchased, or may be produced according to a well-known method or a modification thereof.

Compound (I) has an excellent inhibitory action on heart muscle cell apoptosis and an enhancing action on heart muscle-protecting signals (e.g., enhancing action on gp130 signal, etc.), and is low toxic. The apoptosis of heart muscle cells induced by various causes is usually observed as loss of heart muscle cells in the heart muscle, and have an adverse affect on the cardiac functions. Accordingly, Compound (I) having an inhibitory action on apoptosis of heart muscle cells can be used to protect the cardiac functions from the adverse influence caused by loss of heart muscle cells. Further, Compound (I) can enhance the gp130 signaling pathway, one of signaling pathways for protecting heart muscle cells from apoptosis; and the other signaling pathway different from the gp130 signaling pathway, for example, P13 kinase/Akt pathway (Takihara, "Igaku No Ayumi", vol.194, pp.33–86 (2000)). Thus, Compound (I) can be used to prevent the cardiac functions from being lowered by loss of heart muscle cells.

Compound (I) can be formulated as a pharmaceutical composition in various forms in accordance with a well-known method, and administered orally or parenterally in safety to a mammal (e.g. human, monkey, etc.) to prevent and/or treat heart diseases (e.g., congestive myocardiopathy, hypertrophic obstructive myocardiopathy, hypertrophic non-obstructive myocardiopathy, idiopathic myocardiopathy, angina pectoris, myocardial infarction, poor prognosis of myocardial infarction, chronic cardiac insufficiency, etc.).

Specifically, Compound (I) is mixed with pharmaceutically acceptable carriers and administered orally as tablets, pills, granules, capsules, syrups, emulsions, suspensions, etc. or parenterally, i.e. intravenously, subcutaneously or intramuscularly as injections, suppositories, sublingual tablets. Compound (I) may be administered sublingually, subcutaneously or intramuscularly as sustained-release preparations such as sublingual tablets and microcapsules.

The pharmaceutically acceptable carriers include a wide variety of organic or inorganic carrier materials conventionally used for pharmaceutical preparations, and are mixed, for example, as excipients, lubricants, binders, disintegrators, solvents, solubilizers, suspending agents, isotonizing agents, buffers and soothing agents. If necessary, additives such as preservatives, antioxidants, coloring agents, sweeteners, etc. can also be used.

Preferable examples of the excipients include e.g. lactose, white sugar, D-mannitol, starch, crystalline cellulose and light silicic anhydride. Preferable examples of the lubricants include e.g. magnesium stearate, calcium stearate, talc and colloidal silica. Preferable examples of the binders include e.g. crystalline cellulose, white sugar, D-mannitol, dextrin, hydroxypropyl cellulose, hydroxypropylmethyl cellulose and polyvinyl pyrrolidone. Preferable examples of the disintegrators include e.g. starch, carboxymethyl cellulose, calcium carboxymethyl cellulose, sodium croscarmellose and sodium carboxymethyl starch. Preferable examples of the solvents include e.g. water for injection, alcohol, propylene glycol, Macrogol, sesame oil and corn oil. Preferable examples of the solubilizers include e.g. polyethylene glycol, propylene glycol, D-mannitol, benzyl benzoate, ethanol, trisaminomethane, cholesterol, triethanolamine, sodium carbonate and sodium citrate. Preferable examples of the suspending agents include e.g. surfactants such as stearyl triethanolamine, sodium laurylsulfate, lauryl aminopropionic acid, lecithin, benzalconium chloride, benzetonium chloride and glycerine monostearate; and hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose. Preferable examples of the isotonizing agents include e.g. sodium chloride, glycerine and D-mannitol. Preferable examples of the buffers include e.g. buffers such as phosphates, acetates, carbonates and citrates. Preferable examples of the soothing agents include e.g. benzyl alcohol. Preferable examples of the preservatives include e.g. para-oxybenzoic acid esters, chlorobutanol, benzyl alcohol, phenetyl alcohol, dehydroacetic acid and sorbic acid. Preferable examples of the antioxidants include e.g. sulfites, ascorbic acid.

The does of Compound (I) varies depending on pathological severeness; age, sex and weight of the subject; timing and interval of administration, nature, formulation and type of the pharmaceutical composition; kinds of active ingredients. For treatment of heart diseases, the daily dose for an adult is usually, but not limited to, about 10 μg to 100 mg/kg of body weight, preferably 100 μg to 50 mg/kg of body weight. The daily does is usually divided and administered 1 to 4 times per day.

Compound (I) is present in an amount between about 0.01 and 100% of the total weight of the inhibitor of the present invention.

The present invention will be now further described specifically with reference to the following Reference Examples, Examples, and Experimental Examples, which are however not intended to limit the scope of the present invention.

In the following Reference Examples, "%" means % by weight unless otherwise specified. $^1$H-NMR spectra were measured by Varian GEMINI 200 (200 MHz) spectrometer with tetramethyl silane as the internal standard. All δ values are expressed in ppm.

The abbreviations as used herein have the following meanings.

s: singlet d: doublet dd: double doublet t: triplet q: quartet m: multiplet

J: coupling constant

Hz: Hertz $CDCl_3$: deuterated chloroform $^1$H-NMR: proton nuclear magnetic resonance IR: infrared absorption spectrum

EXAMPLES

Reference Example 1

2-(2-Pyridyl)-4H-1,3-benzothiazin-4-one (Compound 1)

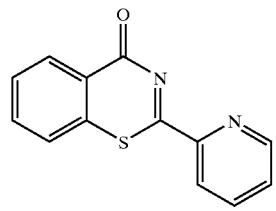

Methyl thiosalicylate (1.6 g, 9.51 mM) and 2-cyanopyridine (1.0 g, 9.60 mM) were dissolved in toluene (2 ml), and then triethylamine (2 ml, 14.4 mM) was added thereto. After heating the mixture under reflux for 8 hours, and the toluene was distilled away. Ethanol was added to the residues, and the resulting precipitates were collected by filtration to give crude crystals (1.7 g). The product was purified by silica gel column chromatography (hexane:chloroform=5:1→chloroform) to give the title compound as crystals (1.0 g, 43.4%).

Elemental Analysis for $C_{13}H_8 N_2OS$ calcd.(%) C, 64.98; H, 3.36; N, 11.66. found (%) C, 64.93; H, 3.31; N, 11.59.

$^1$H-NMR ($CDCl_3$) δ: 7.50–7.75 (m, 4H), 7.85–8.00 (m, 1H), 8.50–8.60 (m, 2H), 8.70–8.80 (m, 1H) IR (KBr): 1660 $cm^{-1}$

Reference Example 2
2-(3-pyridyl)-4H-1,3-benzothiazin-4-one (Compound 2)

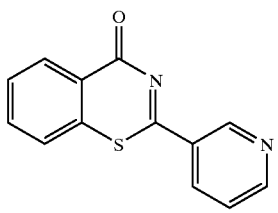

Methyl thiosalicylate (1.8 g, 10.7 mM) and 3-cyanopyridine (1.1 g, 10.56 mM) were dissolved in toluene (5 ml), and then triethylamine (2 ml, 14.4 mM) was added thereto. After heating the mixture under reflux for 48 hours, the same processes as described in Reference Example 1 were performed to give the title compound as crystals (1.1 g, 43.4%).

Elemental Analysis for $C_{13}H_8N_2OS$ calcd.(%) C, 64.98; H, 3.36; N, 11.66. found (%) C, 64.97; H, 3.33; N, 11.63.

Reference Example 3
2-(4-pyridyl)-4H-1,3-benzothiazin-4-one (Compound 3)

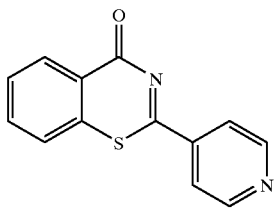

Methyl thiosalicylate (2.0 g, 11.9 mM) and 4-cyanopyridine (1.2 g, 11.5 mM) were dissolved in toluene (5 ml), and then triethylamine (2 ml) was added thereto. After heating the mixture under reflux for 22 hours, the same processes as described in Reference Example 1 were performed to give the title compound as crystals (850 mg, 30.7%).

Elemental Analysis for $C_{13}H_8N_2OS$ calcd.(%) C, 64.98; H, 3.36; N, 11.66. found (%) C, 65.07; H, 3.15; N, 11.62.

Reference Example 4
Ethyl 2-(4-oxo-3,4-dihydro-2H-1,3-benzothiazin-2-ylidene) acetate (Compound 4)

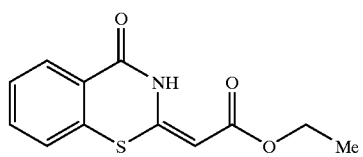

Methyl thiosalicylate (6 g, 35.7 mM) and ethyl cyanoacetate (4 g, 35.4 mM) were dissolved in toluene (10 ml), and then triethylamine (5 ml, 35.8 mM) was added thereto. After heating under reflux for 7 hours, the reaction solution was concentrated. Ethanol was added to the residues and kept still, and the precipitated crystals were collected by filtration to give crude crystals. The product was recrystallized from ethanol to give the title compound as needle crystals (5.4 g, 60.7%).

Elemental Analysis for $C_{12}H_{11}NO_3S$ calcd.(%) C, 57.82; H, 4.45; N, 5.62. found (%) C, 57.86; H, 4.36; N, 5.51.

$^1$H-NMR (CDCl$_3$) δ: 1.31 (t, 3H, J=7.0 Hz), 4.22 (q, 2H, J=7.0 Hz), 5.57 (s, 1H), 7.35 (t, 2H, J=7.4 Hz), 7.50–7.60 (m, 1H), 8.28 (d, 1H, J=7.4 Hz), 9.73 (s, 1H) IR (KBr): 1660, 1590, 1580, 1560, 1440, 1295, 1165, 730 (cm$^{-1}$)

Reference Example 5
2-[2-oxo-2-(1-piperidinyl)ethylidene]-2,3-dihydro-4H-1,3-benzothiazin-4-one (Compound 5)

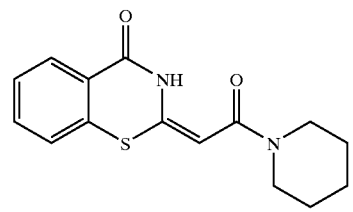

Methyl thiosalicylate (1.7 g, 10.1 mM) and 1-cyanoacetyl piperidine (2.0 g, 13.1 mM) were dissolved in toluene (5 ml), and then triethylamine (2 ml, 14.4 mM) was added thereto. After heating under reflux for 30 hours, the reaction solution was concentrated to give crude crystals. The product was recrystallized from ethanol to give the title compound as needle crystals (730 mg, 25%).

Elemental Analysis for $C_{15}H_{16}N_2O_2S$ calcd.(%) C, 62.48; H, 5.59; N, 9.71. found (%) C, 62.22; H, 5.58; N, 9.65.

$^1$H-NMR (CDCl$_3$) δ: 1.30–1.80 (m, 6H), 3.30–3.70 (m, 4H), 5.30 (s, 1H), 6.90–7.60 (m, 3H), 8.27 (dd, 1H, J=8 Hz, J=2 Hz) IR (KBr): 1660, 1595, 1560 (cm$^{-1}$)

Example 1

Tablets are produced in a conventional manner using Compound 1 (100 mg), lactose (165 mg), corn starch (25 mg), polyvinyl alcohol (4 mg) and magnesium stearate (1 mg).

Experimental Example 1
Inhibitory Activity on Heart Muscle Cell Apoptosis

Newborn rats (within 1 day after birth) were obtained from pregnant Wister rats purchased from Charles River, anesthetized under ether, and sterilized with 70% ethanol, and then their hearts were excised with tweezers. The excised hearts were washed with a phosphate-buffered physiological saline (T900; Takara) and cut into pieces with surgical scissors. These tissue pieces were washed 4 to 5 times with a phosphate-buffered physiological saline to remove a majority of blood-derived non-heart muscle cells. To the tissue pieces derived from 10 newborns, 5 ml of enzyme solution (1.25 mg trypsin (Difco) and 0.25 mg collagenase (Sigma) per ml of phosphate-buffered saline (PBS)) was added and the mixture was stirred with a stirrer at 37° C. for 15 mins. Another 2.5 ml enzyme solution was then added twice repeatedly at a 15-minutes interval. Then, Medium 199 (Gibco) containing 10% fetal calf serum (Biowiker) was added in a half volume of the enzyme solution to terminate the enzyme reaction. The cells were filtered through a Cell Strainer (Falcon) and then centrifuged at 400×g for 5 minutes, whereby the cells were collected.

The cells thus collected from 10 newborns were suspended in 50 ml Medium 199 containing 10% fetal calf serum, plated onto 100 mm Petri dishes (Iwaki) in a volume of 10 ml/dish and cultured for 1 hour in a $CO_2$ incubator set at 5% $CO_2$ and 37° C. The cells were then recovered, filtered through a Cell Strainer and centrifuged at 400×g for 5 minutes to collect the primary heart muscle cells derived from newborn rats.

Then, the heart muscle cells from 10 newborn rats were suspended in 2 ml low-isotonic solution (prepared by dissolving 8.29 g $NH_4Cl$, 1.0 g $KHCO_3$, 37 mg EDTA/2Na (ethylenediaminetetraacetic acid disodium)(Dojindo) in 1 L of water) and left for 3 minutes to disrupt erythrocytes. After 10 ml Medium 199 containing 10% fetal calf serum was added thereto, the primary heart muscle cells from newborn rats were collected by centrifugation at 400×g for 5 minutes. The cells were suspended in Medium 199 containing 10% fetal calf serum and then filtered through a cell strainer. After 0.3% trypan blue was added to, and mildly mixed with, an aliquot of the resulting cell suspension, the number of heart muscle cells was counted on an erythrocyte counting plate.

The primary heart muscle cells from newborn rats were suspended at a density of $3×10^6$ cells/ml in Medium 199 containing 10% fetal calf serum, put onto a 96-well plate in a volume of 0.1 ml/well, and then cultured in a $CO_2$ incubator set at 5% $CO_2$ and 37° C. After the plate was stirred with a micromixer (Taiyo Kagaku Kogyo), the medium was exchanged 3 times with serum-free Medium 199, and then test compounds (Compounds 1 to 5 obtained in Reference Examples) were added thereto. The cells were cultured for additional 4 days to induce apoptosis. Then, fetal calf serum was added thereto at a concentration of 10%, and the cells were further cultured for about 17 hours in a $CO_2$ incubator set at 5% $CO_2$ and 37° C. Finally, the number of viable cells was determined with Cell Counting Kit (Dojindo) using WST-8 (2-(2-methoxy-4-nitrophenyl)-3-(4-nitrophenyl)-5-(2,4-disulfophenyl)-2H-tetrazolium, monosodium salt) as the coloring substrate to determine the inhibition of the heart muscle cell apoptosis.

The above-mentioned exeriment was tripicated in an independent manner.

The Mean minimal effective concentration (±SD) was shown for each test compound (Compounds 1 to 5 obtained in Reference Examples) in Table 1. In Table 1, the minimal effective concentration is defined as the concentration required to increase the mean viable cell number by 30% as compared with that in the absence of test compounds.

TABLE 1

| Compound No. | Minimal Effective Concentration ($\mu$M) |
|---|---|
| 1 | 0.015 ± 0.011 |
| 2 | 0.041 ± 0.018 |
| 3 | 0.014 ± 0.0099 |
| 4 | 0.019 ± 0.0078 |
| 5 | 0.06 ± 0.041 |

This result shows that Compounds 1 to 5 have the inhibitory activiy on heart muscle cell apoptosis.

Experimental Example 2

Confirmation of an Enhancing Action on gp130 Signal

STAT3 (signal transducers and activators of transcription-3) is a primary positive regulatory factor involved in transmission of gp130 signal. Phosphorylation of the tyrosine residue at the 705th position (Tyr705) is essential for activation of STAT3. Accordingly, this phosphorylation can be used as an indicator of activation of STAT3, that is, of an enhancing action on gp130 signal.

Primary heart muscle cells derived from newborn rats were stimulated with a small amount of LIF (Leukemia inhibitory factor) to induce gp130 signal in the presence of a test compound (Compound 1 obtained in Reference Example 1). Phosphorylation of Tyr705 was examined by immunoblotting with an antibody specifically recognizing phosphorylated STAT3, to confirm the enhancing action of the test compound on gp130 signal.

[Method]

The primary heart muscle cells derived from newborn rats, obtained in the method of Experimental Example 1, were suspended at a density of $5×10^6$ cells/ml in Medium 199 containing 10% fetal bovine serum, then put to a 12-well plate (ASAHI TECHNO GLASS CORPORATION) in a volume of 2.0 ml/well, and cultured for 1 day in a 5% $CO_2$ incubator set at 37° C. After the medium was exchanged 3 times with serum-free Medium 199 to remove the serum, the cells were cultured for 24 hours, and then the medium was again exchanged once with serum-free Medium 199, followed by culture for additional 30 to 60 minutes.

A test compound (Compound 1 obtained in Reference Example 1) and human LIF (PEPRO TECH) were added to the thus prepared cells, and incubated for reaction for 30 minutes. The reaction solution was washed 3 times with phosphate buffered physiological saline (1 ml) containing 1 mM sodium orthovanadate (V) (Wako Pure Chemical Industries, Ltd.), and then the cells were treated at 4° C. for 15 minutes with 100 ml cell-lysis buffer [10 mM Tris (hydroxymethyl)aminomethane (Sigma), pH 7.4; 150 mM NaCl; 1 mM EDTA/2Na; 1 mM EGTA (ethylene glycolbis-(2-aminoethylether)-N,N,N',N'-tetraacetic acid)(Sigma); 0.5 mM p-APMSF ((p-aminophenyl)methanesulfonyl fluoride hydrochloride)(Wako Pure Chemical Industries); 200 $\mu$M sodium $\beta$-glycerophosphate n-hydrate (Wako); 20 mM NaF; 2 mM sodium diphosphate decahydrate; 1 mM sodium orthovanadate (V)(Wako); 10 $\mu$g/ml aprotinin (Wako); 10 $\mu$g/ml leupeptin (Peptide Institute, Inc.); 1% Triton X-100; 0.5% Nonident P40 (Fluka); 0.1% SDS (sodium dodesyl sulfate)].

Then, the cells were scratched off with a cell scraper (ASAHI TECHNO GLASS CORPORATION), and the cell-lysis buffer was recovered. The recovered cell-lysis buffer was mixed with an equal volume of a sample buffer (Tris-SDS-$\beta$ME Sample Buffer; Daiichi Pure Chemicals Co., Ltd.) and heated at 95° C. for 5 minutes. This sample was subjected to SDS polyacrylamide electrophoresis on Multi-Gel 7.5 (Daiichi Pure Chemicals). Then, a nitrocellulose membrane (Hybond-ECL; Amersham Pharmacia Biotech) previously immersed for 10 minutes or more in a blotting buffer [0.1 M tris(hydroxymethyl)aminomethane; 0.192 M glycine, 20% ethanol], a blotting filter paper, a dialysis membrane and the gel were placed in Horize Blott (ATTO) to carry out the transfer for 1 hour at 100 mA/gel (6.4 $cm^2$). Thereafter, the blocking of the nitrocellulose membrane was conducted by immersing for 1 hour in a blocking buffer [TTBS buffer (20% Tris-HCl, pH 7.6; 0.137 M NaCl; 0.1% Tween-20) containing 5% skim milk powder (BioRad)] at room temperature under stirring.

Then, the nitrocellulose membrane was immersed in a 1:1000 dilution of primary antibody (anti-phosphorylated STAT3 (Tyr705) antibody; NEW ENGLAND BioLabs) with the blocking buffer, and incubated for reaction at 4° C. for 12 to 18 hours. After the reaction was finished, the membrane was immersed repeatedly 3 times in an appropriate amount (about 80 ml) of TTBS buffer for 5 minutes to remove an excess of the antibody. The membrane was immersed in a 1:2000 dilution of secondary antibody (HRP [horseradish peroxidase] labeled anti-rabbit IgG antibody; NEW ENGLAND BioLabs) with the blocking buffer, and incubated for reaction at room temperature for 1 hour. The membrane was washed in the same manner with about 80 ml TTBS buffer, and a Western blotting detection reagent (ECL+Plus; Amersham) was added in a volume of 6.4 ml/gel (64 $cm^2$), and incubated for reaction at room temperature for 5 minutes, followed by detection with Hyperfilm ECL (Amersham).

[Results]

The results are shown in FIG. 1. In FIG. 1, the 1 st lane from the left shows the phosphorylation in the presence of 10 $\mu$M Compound 1 and 10 U/ml LIF; the 2nd lane from the left shows the phosphorylation in the presence of 1 $\mu$M Compound 1 and 10 U/ml LIF; the 3rd lane from the left shows the phosphorylation in the presence of 0.1 $\mu$M Compound 1 and 10 U/ml LIF; the 4th lane from the left shows the phosphorylation in the presence of 0.01 $\mu$M Compound 1 and 10 U/ml LIF; the 5th lane from the left shows the phosphorylation in the absence of Compound 1 and LIF; the 6th lane from the left shows the phosphorylation in the absence of Compound 1 but the presence of 1000 U/ml LIF and; and the 7th lane from the left shows the phosphorylation in the absence of Compound 1 but the presence of 10 U/ml LIF.

The results confirmed that Compound 1 can further promote phosphorylation of STAT3 induced by 10 U/ml human LIF in primary heart muscle cells derived from newborn rats, and thus that Compound 1 has an enhancing action on gp130 signal.

INDUSTRIAL APPLICABILITY

The inhibitor of heart muscle cell apoptosis of the present invention is low toxic and has an excellent prophylactic and/or therapeutic effect on heart diseases.

What is claimed is:

1. A method for inhibiting heart muscle cell apoptosis in a mammal, comprising administrating an effective amount of a compound represented by the following formula:

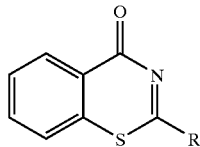

wherein R represents an optionally substituted hydrocarbon group, an optionally substituted aromatic heterocyclic group, or an optionally substituted amino group; or a salt thereof, to said mammal.

2. The method of claim 1 wherein R represents (i) a $C_{1-6}$ alkyl, $C_{3-6}$ cycloalkyl, $C_{4-7}$ cycloalkylalkyl, $C_{2-6}$ alkenyl, $C_{2-6}$ alkynyl, $C_{6-14}$ aryl or $C_{7-16}$ aralkyl, each of which is optionally substituted with 1 to 5 substituents selected from the group consisting of (1) a halogen atom, (2) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, (3) oxo, (4) hydroxy, (5) $C_{1-4}$ alkoxy, (6) carboxy, (7) $C_{1-4}$ alkyl-carbonyl, (8) $C_{6-14}$ aryl-carbonyl, (9) $C_{1-4}$ alkoxy-carbonyl, (10) $C_{6-14}$ aryloxy-carbonyl, (11) $C_{7-16}$ aralkyloxy-carbonyl, (12) carbamoyl, (13) mono-$C_{1-6}$ alkyl-carbamoyl, (14) di-$C_{1-6}$ alkyl-carbamoyl, (15) optionally halogenated $C_{6-14}$ aryl-carbamoyl, (16) 5- or 6-membered heterocyclic carbamoyl, and (17) 5- to 7-membered saturated cyclic amino-carbonyl optionally substituted with $C_{1-3}$ alkyl, phenyl, or benzyl, (ii) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, which is optionally substituted with 1 to 5 substituents selected from the group consisting of (1) a halogen atom, (2) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, (3) oxo, (4) hydroxy, (5) $C_{1-4}$ alkoxy, (6) carboxy, (7) $C_{1-4}$ alkyl-carbonyl, (8) $C_{6-14}$ aryl-carbonyl, (9) $C_{1-4}$ alkoxy-carbonyl, (10) $C_{6-14}$ aryloxy-carbonyl, (11) $C_{7-16}$ aralkyloxy-carbonyl, (12) carbamoyl, (13) mono-$C_{1-6}$ alkyl-carbamoyl, (14) di-$C_{1-6}$ alkyl-carbamoyl, (15) optionally halogenated $C_{1-14}$ aryl-carbamoyl, (16) 5- or 6-membered heterocyclic carbamoyl, and (17) 5- to 7-membered saturated cyclic amino-carbonyl optionally substituted with $C_{1-3}$ alkyl, phenyl, or benzyl, or (iii) an amino or guanidino, each of which is optionally substituted with 1 to 2 substituents selected from the group consisting of (1) a halogen atom, (2) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, (3) oxo, (4) hydroxy, (5) $C_{1-4}$ alkoxy, (6) carboxy, (7) $C_{1-4}$ alkyl-carbonyl, (8) $C_{6-14}$ aryl-carbonyl, (9) $C_{1-4}$ alkoxy-carbonyl, (10) $C_{6-14}$ aryloxy-carbonyl, (11) $C_{7-16}$ aralkyloxy-carbonyl, (12) carbamoyl, (13) mono-$C_{1-6}$ alkyl-carbamoyl, (14) di-$C_{1-6}$ alkyl-carbamoyl, (15) optionally halogenated $C_{6-14}$ aryl-carbamoyl, (16) 5- or 6-membered heterocyclic carbamoyl, and (17) 5- to 7-membered saturated cyclic amino-carbonyl optionally substituted with $C_{1-3}$ alkyl, phenyl, or benzyl.

3. The method of claim 2 wherein R is benzyl, benzoylmethyl, 3-pyridylaminocarbonylmethyl, 4-chlorophenylaminocarbonylmethyl, ethoxycarbonylmethyl, piperidinocarbonylmethyl, 2-pyridyl, 3-pyridyl, 4-pyridyl, 3-hydroxy-2-benzo[b]furanyl, or guanidino.

4. The method of claim 1 wherein the aromatic heterocyclic group is 2-pyridyl, 3-pyridyl or 4-pyridyl.

5. A method for preventing and/or treating heart disease in a mammal comprising administering an effective amount of a compound represented by the following formula:

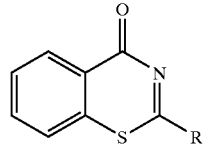

wherein R represents an optionally substituted hydrocarbon group, an optionally substituted aromatic heterocyclic group, or an optionally substituted amino group; or a salt thereof, to said mammal.

6. The method of claim 5 wherein R represents (i) a $C_{1-6}$ alkyl, $C_{3-6}$ cycloalkyl, $C_{4-7}$ cycloalkylalkyl, $C_{2-6}$ alkenyl, $C_{2-6}$ alkynyl, $C_{6-14}$ aryl or $C_{7-16}$ aralkyl, each of which is optionally substituted with 1 to 5 substituents selected from the group consisting of (1) a halogen atom, (2) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, (3) oxo, (4) hydroxy, (5) $C_{1-4}$ alkoxy, (6) carboxy, (7) $C_{1-4}$ alkyl-carbonyl, (8) $C_{6-14}$ aryl-carbonyl, (9) $C_{1-4}$ alkoxy-carbonyl, (10) $C_{6-14}$ aryloxy-carbonyl, (11) $C_{7-16}$ aralkyloxy-carbonyl, (12) carbamoyl, (13) mono-$C_{1-6}$ alkyl-carbamoyl, (14) di-$C_{1-6}$ alkyl-carbamoyl, (15) optionally halogenated $C_{6-14}$ aryl-carbamoyl, (16) 5- or 6-membered heterocyclic carbamoyl, and (17) 5- to 7-membered saturated cyclic amino-carbonyl optionally substituted with $C_{1-3}$ alkyl, phenyl, or benzyl, (ii) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, which is optionally substituted with 1 to 5 substituents selected from the group consisting of (1) a halogen atom, (2) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, (3) oxo, (4) hydroxy, (5) $C_{1-4}$ alkoxy, (6) carboxy, (7) $C_{1-4}$ alkyl-carbonyl, (8) $C_{6-14}$ aryl-carbonyl, (9) $C_{1-4}$ alkoxy-carbonyl, (10) $C_{6-14}$ aryloxy-carbonyl, (11) $C_{7-16}$ aralkyloxy-carbonyl, (12) carbamoyl, (13) mono-$C_{1-6}$ alkyl-carbamoyl, (14) di-$C_{1-4}$ alkyl-carbamoyl, (15) optionally halogenated $C_{6-4}$ aryl-carbamoyl, (16) 5- or 6-membered heterocyclic carbamoyl, and (17) 5- to 7-membered saturated cyclic amino-carbonyl optionally substituted with $C_{1-3}$ alkyl, phenyl, or benzyl, or (iii) an amino or guanidino, each of which is optionally substituted with 1 to 2 substituents selected from the group consisting of (1) a halogen atom, (2) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, (3) oxo, (4) hydroxy, (5) $C_{1-4}$ alkoxy, (6) carboxy, (7) $C_{1-4}$ alkyl-carbonyl, (8) $C_{6-14}$ aryl-carbonyl, (9) $C_{1-4}$ alkoxy-carbonyl, (10) $C_{6-4}$ azyloxy-carbonyl, (11) $C_{7-16}$ aralkyloxy-carbonyl, (12) carbamoyl, (13) mono-$C_{1-6}$ alkyl-carbamoyl, (14) di-$C_{1-6}$ alkyl-carbamoyl, (15) optionally halogenated $C_{6-14}$ aryl-carbamoyl, (16) 5- or 6-membered heterocyclic carbamoyl, and (17) 5- to 7-membered saturated cyclic amino-carbonyl optionally substituted with $C_{1-3}$ alkyl, phenyl, or benzyl.

7. The method of claim 6 wherein R is benzyl, benzoylmethyl, 3-pyridylaminocarbonylmethyl, 4-chlorophenylaminocarbonylmethyl, ethoxycarbonylmethyl, piperidinocarbonylmethyl, 2-pyridyl, 3-pyridyl, 4-pyridyl, 3-hydroxy-2-benzo[b]furanyl, or guanidino.

8. The method of claim 5 wherein the aromatic heterocyclic group is 2-pyridyl, 3-pyridyl or 4-pyridyl.

9. A method for enhancing gp130 signals in a mammal comprising administering an effective amount of a compound represented by the following formula:

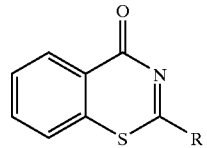

wherein R represents an optionally substituted hydrocarbon group, an optionally substituted aromatic heterocyclic group, or an optionally substituted amino group; or a salt thereof, to said mammal.

10. The method of claim 9 wherein R represents (i) a $C_{1-6}$ alkyl, $C_{3-6}$ cycloalkyl, $C_{4-7}$ cycloalkylalkyl, $C_{2-6}$ alkenyl, $C_{2-5}$ alkynyl, $C_{6-14}$ aryl or $C_{7-16}$ aralkyl, each of which is optionally substituted with 1 to 5 substituents selected from the group consisting of (1) a halogen atom, (2) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, (3) oxo, (4) hydroxy, (5) $C_{1-4}$ alkoxy, (6) carboxy, (7) $C_{1-4}$ alkyl-carbonyl, (8) $C_{6-14}$ aryl-carbonyl, (9) $C_{1-4}$ alkoxy-carbonyl, (10) $C_{6-14}$ aryloxy-carbonyl, (11) $C_{7-16}$ aralkyloxy-carbonyl, (12) carbamoyl, (13) mono-$C_{1-6}$ alkyl-carbamoyl, (14) di-$C_{1-6}$ alkyl-carbamoyl, (15) optionally halogenated $C_{6-14}$ aryl-carbamoyl, (16) 5- or 6-membered heterocyclic carbamoyl, and (17) 5- to 7-membered saturated cyclic amino-carbonyl optionally substituted with $C_{1-3}$ alkyl, phenyl, or benzyl, (ii) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, which is optionally substituted with 1 to 5 substituents selected from the group consisting of (1) a halogen atom, (2) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, (3) oxo, (4) hydroxy, (5) $C_{1-4}$ alkoxy, (6) carboxy, (7) $C_{1-4}$ alkyl-carbonyl, (8) $C_{6-14}$ aryl-carbonyl, (9) $C_{1-4}$ alkoxy-carbonyl, (10) $C_{6-14}$ aryloxy-carbonyl, (11) $C_{7-16}$ aralkyloxy-carbonyl, (12) carbamoyl, (13) mono-$C_{1-6}$ alkyl-carbamoyl, (14) di-$C_{1-6}$ alkyl-carbamoyl, (15) optionally halogenated $C_{1-14}$ aryl-carbamoyl, (16) 5- or 6-membered heterocyclic carbamoyl, and (17) 5- to 7-membered saturated cyclic amino-carbonyl optionally substituted with $C_{1-3}$ alkyl, phenyl, or benzyl, or (iii) an amino or guanidino, each of which is optionally substituted with 1 to 2 substituents selected from the group consisting of (1) a halogen atom, (2) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, (3) oxo, (4) hydroxy, (5) $C_{1-4}$ alkoxy, (6) carboxy, (7) $C_{1-4}$ alkyl-carbonyl, (8) $C_{6-14}$ aryl-carbonyl, (9) $C_{1-4}$ alkoxy-carbonyl, (10) $C_{6-14}$ aryloxy-carbonyl, (11) $C_{7-16}$ aralkyloxy-carbonyl, (12) carbamoyl, (13) mono-$C_{1-6}$ alkyl-carbamoyl, (14) di-$C_{1-6}$ alkyl-carbamoyl,

(15) optionally halogenated $C_{6-14}$ aryl-carbamoyl, (16) 5- or 6-membered heterocyclic carbamoyl, and (17) 5- to 7-membered saturated cyclic amino-carbonyl optionally substituted with $C_{1-3}$ alkyl, phenyl, or benzyl.

11. The method of claim 10 wherein R is benzyl, benzoylmethyl, 3-pyridylaminocarbonylmethyl, 4-chlorophenylaminocarbonylmethyl, ethoxycarbonylmethyl, piperidinocarbonylmethyl, 2-pyridyl, 3-pyridyl, 4-pyridyl, 3-hydroxy-2-benzo[b]furanyl, or guanidino.

12. The method of claim 9 wherein the aromatic heterocyclic group is 2-pyridyl, 3-pyridyl or 4-pyridyl.

13. A method for enhancing heart muscle protection signals in a mammal comprising administering an effective amount of a compound represented by the following formula:

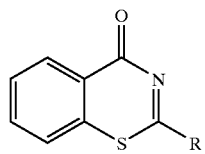

wherein R represents an optionally substituted hydrocarbon group, an optionally substituted aromatic heterocyclic group, or an optionally substituted amino group; or a salt thereof, to said mammal.

14. The method of claim 13 wherein R represents (i) a $C_{1-6}$ alkyl, $C_{3-6}$ cycloalkyl, $C_{4-7}$ cycloalkylalkyl, $C_{2-6}$ alkenyl, $C_{2-5}$ alkynyl, $C_{6-14}$ aryl or $C_{7-16}$ aralkyl, each of which is optionally substituted with 1 to 5 substituents selected from the group consisting of (1) a halogen atom, (2) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, (3) oxo, (4) hydroxy, (5) $C_{1-4}$ alkoxy, (6) carboxy, (7) $C_{1-4}$ alkyl-carbonyl, (8) $C_{6-14}$ aryl-carbonyl, (9) $C_{1-4}$ alkoxy-carbonyl, (10) $C_{6-14}$ aryloxy-carbonyl, (11) $C_{7-16}$ aralkyloxy-carbonyl, (12) carbamoyl, (13) mono-$C_{1-6}$ alkyl-carbamoyl, (14) di-$C_{1-6}$ alkyl-carbamoyl, (15) optionally halogenated $C_{6-14}$ aryl-carbamoyl, (16) 5- or 6-membered heterocyclic carbamoyl, and (17) 5- to 7-membered saturated cyclic amino-carbonyl optionally substituted with $C_{1-3}$ alkyl, phenyl, or benzyl, (ii) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, which is optionally substituted with 1 to 5 substituents selected from the group consisting of (1) a halogen atom, (2) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, (3) oxo, (4) hydroxy, (5) $C_{1-4}$ alkoxy, (6) carboxy, (7) $C_{1-4}$ alkyl-carbonyl, (8) $C_{6-14}$ aryl-carbonyl, (9) $C_{1-4}$ alkoxy-carbonyl, (10) $C_{6-14}$ aryloxy-carbonyl, (11) $C_{7-16}$ aralkyloxy-carbonyl, (12) carbamoyl, (13) mono-$C_{1-6}$ alkyl-carbamoyl, (14) di-$C_{1-6}$ alkyl-carbamoyl, (15) optionally halogenated $C_{1-14}$ aryl-carbamoyl, (16) 5- or 6-membered heterocyclic carbamoyl, and (17) 5- to 7-membered saturated cyclic amino-carbonyl optionally substituted with $C_{1-3}$ alkyl, phenyl, or benzyl, or (iii) an amino or guanidino, each of which is optionally substituted with 1 to 2 substituents selected from the group consisting of (1) a halogen atom, (2) an aromatic heterocyclic group selected from the group consisting of thienyl, furyl, pyridyl, quinolyl, isoquinolyl, pyrazinyl, pyrimidinyl, pyrrolyl, imidazolyl, pyridazinyl, isothiazolyl, isooxazolyl, indolyl, benzothiazolyl, benzothienyl, and benzofuranyl, (3) oxo, (4) hydroxy, (5) $C_{1-4}$ alkoxy, (6) carboxy, (7) $C_{1-4}$ alkyl-carbonyl, (8) $C_{6-14}$ aryl-carbonyl, (9) $C_{1-4}$ alkoxy-carbonyl, (10) $C_{6-14}$ aryloxy-carbonyl, (11) $C_{7-16}$ aralkyloxy-carbonyl, (12) carbamoyl, (13) mono-$C_{1-6}$ alkyl-carbamoyl, (14) di-$C_{1-6}$ alkyl-carbamoyl, (15) optionally halogenated $C_{6-14}$ aryl-carbamoyl, (16) 5- or 6-membered heterocyclic carbamoyl, and (17) 5- to 7-membered saturated cyclic amino-carbonyl optionally substituted with $C_{1-3}$ alkyl, phenyl, or benzyl.

15. The method of claim 14 wherein R is benzyl, benzoylmethyl, 3-pyridylaminocarbonylmethyl, 4-chlorophenylaminocarbonylmethyl, ethoxycarbonylmethyl, piperidinocarbonylmethyl, 2-pyridyl, 3-pyridyl, 4-pyridyl, 3-hydroxy-2-benzo[b]furanyl, or guanidino.

16. The method of claim 13 wherein R is an optionally substituted aromatic heterocyclic group, and said aromatic heterocyclic group is 2-pyridyl, 3-pyridyl or 4-pyridyl.

* * * * *